United States Patent [19]

Gelfand

[11] 4,049,727
[45] Sept. 20, 1977

[54] POLYHALOINDENE COMPOUNDS

[75] Inventor: Samuel Gelfand, Lewiston, N.Y.

[73] Assignee: Hooker Chemicals & Plastics Corporation, Niagara Falls, N.Y.

[21] Appl. No.: 612,072

[22] Filed: Sept. 10, 1975

Related U.S. Application Data

[63] Continuation-in-part of Ser. No. 401,931, Sept. 28, 1973, abandoned.

[51] Int. Cl.$^2$ .............................................. C07C 25/14
[52] U.S. Cl. .............................. 260/650 R; 260/651 R
[58] Field of Search .......................... 260/650 R, 651 R

[56] References Cited

U.S. PATENT DOCUMENTS

| 2,745,884 | 5/1956 | Kundiger et al. | 260/650 R |
| 2,786,062 | 3/1957 | Vollmann | 260/650 R |
| 3,716,591 | 2/1973 | Brady | 260/650 R |
| 3,723,473 | 3/1973 | Schmerling | 260/650 R |
| 3,872,054 | 3/1975 | Shaw | 260/650 R |

OTHER PUBLICATIONS

Zincke et al., Liebig's Annalen 272 243, 267 and 270 (1892).
Adams et al., Chem. Abstracts 77 151336e (1972).
Balester et al., Chem. Abstracts 55 19876b (1961).

*Primary Examiner*—C. Davis
*Attorney, Agent, or Firm*—Peter F. Casella; William J. Crossetta, Jr.; Arthur S. Cookfair

[57] ABSTRACT

New compounds and a process for the preparation thereof are disclosed of the formula:

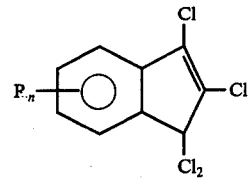

wherein each R is independently halogen or lower alkyl and $n$ is from 2 to 4. These compounds are useful as chemical intermediates and fire retardant additives.

12 Claims, No Drawings

POLYHALOINDENE COMPOUNDS

This is a continuation-in-part of copending application Ser. No. 401,931, filed Sept. 28, 1973 now abandoned.

BACKGROUND OF THE INVENTION

In recent years the development of fire retardant compounds has become of considerable commercial importance in that such articles as castings, moldings, foamed or laminated articles, etc., are required, or at least desired, to be resistant to fire and flame and to possess the ability to endure heat without extensive deterioration. Typical illustrations of applications of such compounds include castings for live electrical contacts which should not be ignited by flame or sparks, structural members such as pipes, wall coverings, wall paneling, windows, etc., and such items as ash trays, waste baskets, fibers and the like.

The use of certain additives for the purpose of reducing the flammability of various substrates is well known to those skilled in the art. Among the additives currently employed for such a use are various specific types of phosphorus containing compounds. These phosphorus compounds are generally used alone or in combination with other materials. Certain analogous materials such as chlorostyrene copolymers, chlorinated paraffin waxes, alone or with antimony oxide or phosphorus compounds are also known to be effective flame retardants for resinous materials.

It is an object of the instant invention to provide useful flame retardant compounds. It is also an object of this invention to provide intermediates for the preparation of other chemical compounds. It is a further object of this invention to provide a process for the production of polyhaloindenes in high yields and high purity. Further, it is an object of the instant invention to provide a process for the preparation of polyhaloindene intermediates useful for the production of other compounds. It is still another object of this invention to provide a simple process for the production of polyhaloindenes. These and other objects will become more apparent from the following discussion.

SUMMARY OF THE INVENTION

In accordance with this invention, new compounds of the formula,

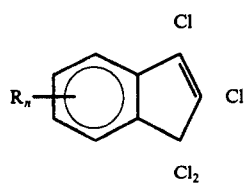

wherein each R is independently selected from the group consisting of chlorine, bromine, fluorine and lower alkyl and $n$ is from 2 to 4, provided that when every R is chlorine, $n$ is from 2-3, are prepared by a process which comprises reacting a substituted aromatic of the formula:

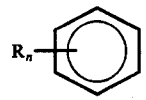

wherein R and $n$ are as hereinbefore defined, providing there is unsubstitution on at least two adjacent carbon atoms of the aromatic, with hexachloropropylene in the presence of ferric chloride, the reaction being set out as follows:

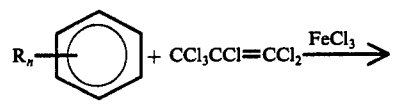

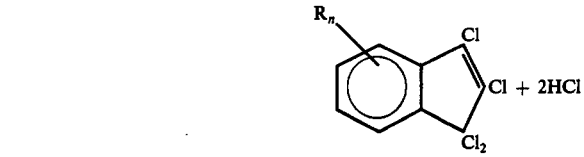

Illustrative of the substituted aromatic compounds, which may be utilized as halo aromatic reactants for the process of the present invention, are: ortho, meta and para-dichlorobenzene 1,2,4, trichlorobenzene, 1,2,3, trichlorobenzene, 1,2,3,4 tetrachlorobenzene, 2,3, dichlorotoluene, 2,4, dichlorotoluene, 2,5, dichloro toluene, 2,6, dichlorotoluene, 3,4, dichlorotoluene, para-chlorotoluene, ortho-chlorotoluene, paradibromobenzene, and the like. Other substituted aromatic hydrocarbons of the type described herein which will not adversely affect the reaction mechanism can be employed. Only a catalytic amount of ferric chloride is required, generally such being in the range of about 0.01 to about 10 mole percent with the preferred range being about 1 to about 6 mole percent.

The reaction is generally accomplished by heating the reactants in the presence of the ferric chloride catalyst until the reaction is complete as evidenced by the evolution of the required amount of hydrogen halide. The reaction temperature will vary with the reactants being employed, but generally has a range of about 25° C. to about 200° C., with the preferred range being from about 50° C. to about 160° C.

A solvent is not generally necessary to produce the compounds of the instant invention but one can be used to moderate or facilitate the reaction. Among the solvents which can be used are perchloroethylene, carbon tetrachloride, octachlorocyclopentene, hexachlorobutadiene, and the like. Other solvents of higher boiling point wich maintain the required reaction temperature and do not react with either the selected reactants or the catalysts to adversely affect the reaction mechanism can also be employed. The use of solvents, such as perchloroethylene or carbon tetrachloride, will usually require a higher operating temperature. Thus, for any particular reaction, the temperature selected will generally depend upon the solvent and the reactivity of the reactants. The reaction product is isolated by methods known in the art, e.g., in the case of liquid products, the catalyst is removed by washing with aqueous hydrochloric acid, and the product is isolated by distillation. Solids may be conveniently isolated by triturating the reaction mixture with acetone to remove the catalysts and thereafter filtering the solid product.

In order that those skilled in the art may better understand the present invention in the manner in which it may be practiced, the following illustrative examples are given.

In the specification, examples and claims, parts are by weight and temperatures are in degrees centigrade unless otherwise stated.

EXAMPLE I

Preparation of Heptachloroindene

A mixture containing 125 grams (0.5 mole) of hexachloropropylene, 91 grams (0.5 moles) of 1,2,4-trichlorobenzene and 5 grams of ferric chloride was charged to a 500 milliliter 3 necked flask equipped with stirrer, thermometer, and water condenser leading to a water trap for absorbing hydrogen chloride. The mixture was stirred and heated at about 130° to 145° C. for 2 hours during which time 17.8 grams of hydrogen chloride evolved and was collected. The reaction mixture was then washed with concentrated hydrochloric acid, then with water, dried over calcium carbonate and filtered. The filtrate was distilled under vacuum and yielded 66 grams of product boiling at about 146° C. to 157° C. at 0.3 milliliters of mercury pressure. The product solidified on standing and analyzed for $C_9HCl_7$:

|  | Theoretical | Found |
|---|---|---|
| % Chlorine | 69.5 | 68.9 |

EXAMPLE 2

Reaction of Hexachloropropylene and 2,4-dichlorotoluene

A mixture containing 50 grams (0.2 mole) of hexachloropropylene, 32 grams (0.2 mole) of 2,4-dichlorotoluene, and 1 gram of ferric chloride was heated at about 60° C. to about 120° C. for 4 hours by the method of Example I, during which time 11.9 grams of hydrogen chloride evolved and was collected. The mixture was then triturated with acetone and filtered yielding 41.7 grams of product. Upon double extraction of this product first with acetone and then with methanol two isomers of methylhexachloroindene were separated and identified by elemental, infrared and NMR spectrum analysis. The results are as indicated below.

|  | Theoretical | Isomer A (Found) | Isomer B (Found) |
|---|---|---|---|
| % Carbon | 35.65 | 35.50 | 35.50 |
| % H | 1.20 | 1.20 | 1.17 |
| % Cl | 63.1 | 62.7 | 62.7 |
| Melting Point | — | 134–137° C. | 149.5–150° C |

EXAMPLE 3

Using the method of Example I, hexachloropropylene was reacted in a 1:1 molar ratio with a series of substituted aromatics. The results were shown in Table I.

TABLE I

| Aromatic | Reaction Temp(° C.) | Time (Hr.) | Product | % Yield |
|---|---|---|---|---|
| 1,2,3,4-tetrachlorobenzene | 150–160 | 8 | Octachloroindene | 8.4 |
| 3,4-dichlorotoluene | 120–130 | 5 | Methylhexachloroindene | 21.2 |
| m-dichlorobenzene | 95–100 | 4 | Hexachloroindene | 22.8 |

EXAMPLE 4

Reaction of Hexachloropropylene and Ortho-Dichlorobenzene

A mixture containing 29.4 grams (0.2 mole), of ortho-dichlorobenzene, 50 grams (0.2 moles) of hexachloropropylene and 2.5 grams of ferric chloride in 250 milliliters of perchloroethylene was heated and stirred by the process of Example I for about 4 hours at reflux (125° C.). The reaction mixture was then washed with concentrated hydrochloric acid, then water and distilled to give a 48.7% yield of hexachloroindene. The product was confirmed by infrared and NMR spectra analysis as structured.

EXAMPLE 5

Preparation of Nonachloroindane 26.7 grams of heptachloroindene was dissolved in 100 milliliters of carbon tetrachloride and chlorinated with gaseous chlorine in the presence of ultra violet light catalyzed at about 60° C. for about 12 hours. The product was distilled to remove the carbon tetrachloride solvent and a quantitative yield of 1,1,2,2,3,3,4,6,7-nonachloroindane was obtained and identified by IR and NMR spectrographic analysis.

EXAMPLE 6

Pencil rod test specimens were prepared having the following compositions:

Specimen 1

70% high impact polystyrene
6% antimony oxide
24% heptachloroindene

Specimen 2

70% high impact polystyrene
6% antimony oxide
24% nonachloroindane

Specimen 3

70% high impact polystyrene
6% antimony oxide
24% hexachloroindene

Specimen 4

70% acrylonitrile-butadiene-styrene
6% antimony oxide
24% heptachloroindene

Specimen 5

70% acrylonitrile-butadiene-styrene
6% antimony oxide
24% nonachloroindane

Specimen 6

70% acrylonitrile-butadiene-styrene
6% antimony oxide
24% hexachloroindene

Each specimen was then subjected to ASTM test D-635 to determine its fire retardant effects with results as indicated in Table II.

TABLE II

| Specimen | Flame Out Time(Sec.) | Afterglow(sec.) |
|---|---|---|
| 1 | 0 | ≈30 |
| 2 | 0 | 0 |
| 3 | 0 | 18 |

TABLE II-continued

| Specimen | Flame Out Time(Sec.) | Afterglow(sec.) |
|---|---|---|
| 4 | 5 | 0 |
| 5 | 1 | 3 |
| 6 | 4 | 11 |

Each of the specimens did not drip or flow when subjected to the test and are classified as self-extinguishing. Oxygen Index measurements were taken of each specimen and each showed indices within the range of 29-33.

I claim:

1. Compounds of the formula:

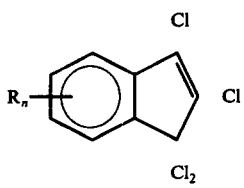

wherein R is independently selected from the group consisting of chlorine, bromine, fluorine, and lower alkyl and $n$ is 2 to 4 providing when every R is chlorine, $n$ is from 2-3.

2. The compound of claim 1 wherein each R is chlorine.

3. The compound of claim 2 wherein $n$ is 3.

4. The compound of claim 1 wherein $n$ is 3 and one R is methyl, and two R's are each chlorine.

5. A process for the preparation of compounds of the formula:

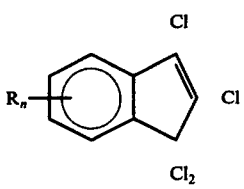

wherein each R is independently halogen or lower alkyl and $n$ is 2 to 4, comprising reacting a substituted aromatic of the formula

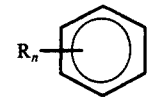

wherein each R is independently selected from the group consisting of chlorine, bromine, fluorine and lower alkyl and $n$ is from 2 to 4 providing there is unsubstitution on at least two adjacent carbon atoms of the aromatic, with hexachloropropylene in the presence of a catalytic amount of ferric chloride.

6. The process of claim 5 wherein said substituted aromatic is selected from the group consisting of ortho, meta and paradichlorobenzene, 1,2,4, trichlorobenzene, 1,2,3, trichlorobenzene, 1,2,3,4, tetrachlorobenzene, 2,3, dichlorotoluene, 2,4, dichlorotoluene, 2,5, dichlorotoluene, 2,6, dichlorotoluene, 3,4, dichlorotoluene, para-chlorotoluene, ortho-chlorotoluene, and para-dibromobenzene.

7. The process of claim 5 wherein said reaction is maintained at about 25° C. to about 200° C.

8. The process of claim 2 wherein said reaction is maintained at from about 50° C. to about 160° C.

9. The process of claim 5 wherein about 0.01 to about 10 mole percent of ferric chloride is present.

10. The process of claim 9 wherein from about 1 to about 6 mole percent of ferric chloride is present.

11. The process of claim 5 wherein a solvent which maintains the required reaction temperature and does not react with either the selected reactants or the catalysts to adversely affect the reaction mechanism is additionally present.

12. The process of claim 11 wherein said solvent is selected from the group consisting of perchloroethylene, carbon tetrachloride, octachlorocyclopentene and hexachlorobutadiene.

* * * * *